US008323670B2

(12) United States Patent
Pisak et al.

(10) Patent No.: US 8,323,670 B2
(45) Date of Patent: Dec. 4, 2012

(54) TOPICAL COMPOSITIONS OF OPIOID ANTAGONISTS AND METHODS FOR TREATING SKIN CONDITIONS THEREWITH

(75) Inventors: Ibrahim Mustafa Iskender Pisak, Istanbul (TR); Semra Bingol, Istanbul (TR); Mehmet Levent Selamoglu, Istanbul (TR); Nevhiz Pak, Istanbul (TR)

(73) Assignee: Ak Kimya Ithalat-Ihracat Ve Sanayii A.S., Istanbul (TR)

( * ) Notice: Subject to any disclaimer, the term of this patent is extended or adjusted under 35 U.S.C. 154(b) by 0 days.

(21) Appl. No.: 12/892,046

(22) Filed: Sep. 28, 2010

(65) Prior Publication Data

US 2011/0082167 A1    Apr. 7, 2011

(30) Foreign Application Priority Data

Oct. 1, 2009   (TR) .................................. 2009 07463

(51) Int. Cl.
*A61K 9/00* (2006.01)
*A61K 31/44* (2006.01)

(52) U.S. Cl. ........................................ 424/400; 514/282
(58) Field of Classification Search .................. 424/400; 514/282
See application file for complete search history.

(56) References Cited

U.S. PATENT DOCUMENTS

| | | | | |
|---|---|---|---|---|
| 4,416,886 A * | 11/1983 | Bernstein | ...................... | 514/282 |
| 4,888,346 A | 12/1989 | Bihari et al. | | |
| 5,356,900 A | 10/1994 | Bihari et al. | | |
| 6,248,365 B1 | 6/2001 | Romisch et al. | | |
| 6,355,245 B1 | 3/2002 | Evans et al. | | |
| 6,384,044 B1 | 5/2002 | Bihari | | |
| 6,538,028 B1 | 3/2003 | Pierson, III et al. | | |
| 2003/0077301 A1* | 4/2003 | Maibach et al. | .............. | 424/400 |
| 2003/0235542 A1* | 12/2003 | Maibach et al. | ................ | 424/62 |
| 2003/0235627 A1* | 12/2003 | Maibach et al. | .............. | 424/682 |
| 2006/0002874 A1* | 1/2006 | Maibach et al. | ................ | 424/62 |
| 2011/0082167 A1 | 4/2011 | Pisak et al. | | |
| 2011/0165232 A1 | 7/2011 | Pisak et al. | | |
| 2011/0245278 A1 | 10/2011 | Pisak et al. | | |

FOREIGN PATENT DOCUMENTS

WO    WO 2010/032073    3/2010

OTHER PUBLICATIONS

I.S. Zagon & P.J. McLaughlin, "Naltrexone modulates tumor response in mice with neuroblastoma", *Science*, 221: 671-3 (Aug. 12, 1983).
E.A. Moore & S. Wilkinson, The Promise of Low Dose Naltrexone Therapy: Potential Benefits in Cancer, Autoimmune, Neurological and Infectious Disorders (McFarland & Company, Inc., Publishers, 2009)—Table of Contents.
Herpes zoster opthalmicus, The Merck manual of diagnosis and therapy, The Merck manuals online medical library. http://www.merck.com/mmpe/sec09/ch102/ch102e.html#sec09-ch102-ch102e-355, Oct. 2008.
Silman A. J., "Mortality from scleroderma in England and Wales 1968-1975," *Ann. Rheu. Dis.* 50: 95-96 (1991).
Smith, Textbook of the Autoimmune Diseases, Edited by Lahita, Chiorazzi and Reeves, Lippincott Williams & Wilkins, Philadelphia 2000—Table of Contents.
Clements P. J. and Furst D. E. (1996) "Systemic Sclerosis" Williams and Williams, Baltimore—Table of Contents.
Strehlow D. and Korn J, "Biology of the scleroderma fibroblast." *Curr. Opin. Rheumatol.* 10: 572-578 (1998).
LeRoy E. C., "Increased collagen synthesis by scleroderma skin fibroblasts in vitro," *J. Clin. Invest.* 54: 880-889 (1974).
Martini, Maccado, Ravelli et al., *Arthritis Rheum.* 42: 807-811 (1999).
"Risk factors associated with age-related macular degeneration—a case-control study in the age-related eye disease study: Report No. 3," *Ophthalmology*, 107 (12): 2224-2232 (2000).
Van der Schaft TL, de Bruijn WC, Mooy CM, Ketelaars DA, de Jong PT, "Element analysis of the early stages of age-related macular degeneration," *Arch. Ophthalmol.*, 110(3): 389-94 (1992).
Lengyel I, Flinn JM, Peto T, et al. "High concentration of zinc in sub-retinal pigment epithelial deposits," *Exp. Eye Res.*, 84(4): 772-80 ( 2007).
Hageman GS, Luthert PJ, Victor Chong NH, Johnson LV, Anderson DH, Mullins RF, "An integrated hypothesis that considers drusen as biomarkers of immune-mediated processes at the RPE-Bruch's membrane interface in aging and age-related macular degeneration," *Prog Retin Eye Res.*, 20 (6): 705-732 (2001).
Patel N, Adewoyin T, Chong NV, "Age-related macular degeneration: a perspective on genetic studies", *Eye*, 22(6):768-776 (2008).
Zagon IS, Rahn KA, McLaughlin PJ , (2007) "Opioids and migration, chemotaxis, invasion, and adhesion of human cancer cells". *Neuropeptides*, 41 (6) : 441-452.
J.C. Ballantyne, J. Mao, "Opioid Therapy for Chronic Pain," *N. Eng. J. Med.* 349: 1943-1953 (Nov. 13, 2003).
U.S. Appl. No. 13/076,564, filed Mar. 31, 2011, entitled *Compositions of Opioid Antagonists and Methods for Treating Conditions Caused by the Varicella-Zoster Virus Therewith*, and currently assigned to USPTO.
U.S. Appl. No. 13/076,590, filed Mar. 31, 2011, entitled *Compositions of Opioid Antagonists and Methods for Treating Scleroderma Therewith*, and currently assigned to USPTO.
Herpes zoster opthalmicus, The Merck manual of diagnosis and theraphy, The Merck manuals online medical library. http://www.merck.com/mmpe/sec09/ch102/ch102e.html#sec09-ch102-ch102e-355, Accessed Jan. 6, 2010.
The eye digest, (2007) Eye & Ear Infirmary, University of Illinois. http://www.agingeye.net/maculardegen/maculardegennewdevelopments.php. Accessed May 24, 2012.

* cited by examiner

*Primary Examiner* — Shengjun Wang
(74) *Attorney, Agent, or Firm* — Wilson Sonsini Goodrich & Rosati PC

(57) ABSTRACT

Provided are topical compositions comprising opioid antagonists, such as naltrexone or naloxone, or their pharmaceutically acceptable salts, and methods for treating skin conditions, such as those caused by human papillomavirus, therewith.

22 Claims, No Drawings

TOPICAL COMPOSITIONS OF OPIOID ANTAGONISTS AND METHODS FOR TREATING SKIN CONDITIONS THEREWITH

CROSS-REFERENCE TO RELATED APPLICATIONS

This application claims the benefit of priority to Turkish patent application No. 2009/07463, filed on Oct. 1, 2009, the contents of which are herein incorporated by reference in their entirety.

FIELD OF THE INVENTION

The invention relates to topical compositions comprising opioid antagonists, such as naltrexone or naloxone, or their pharmaceutically acceptable salts, and methods for treating skin conditions, such as those caused by human papillomavirus, therewith.

BACKGROUND OF THE INVENTION

Naltrexone has the chemical name morphinan-6-one, 17-(cyclopropylmethyl)-4,5-epoxy-3,14-dihydroxy-(5α). The molecular formula of naltrexone is $C_{20}H_{23}NO_4$ and its molecular weight is 341.41 in the anhydrous form (<1% maximum water content). The chemical structure of naltrexone is shown below.

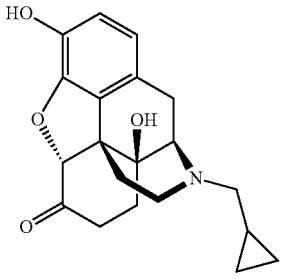

Naltrexone

Naltrexone has been approved for use in the treatment of alcoholism or narcotic addiction. It is believed that naltrexone functions by blocking the brain receptors that trigger the effects of alcohol or narcotics. Naltrexone is marketed by Durmed in the form of a tablet under the tradename ReVia® and by Alkermes in the form of a powder for injectable suspension under the tradename Vivitrol®.

Naloxone has the chemical name (−)-17-allyl-4,5α-epoxy-3,14-dihydroxymorphinan-6-one and the molecular formula $C_{19}H_{21}NO_4$. The chemical structure of naloxone is shown below.

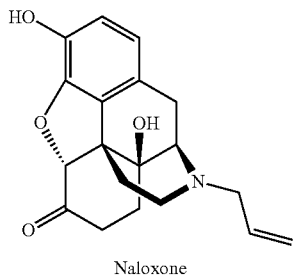

Naloxone

In the early 1980s, it was reported that the administration of low dose naltrexone (less than 10 mg naltrexone per day) increases the production of endogenous endomorphins, especially the endogenous pentapeptide metenkephalin, and increases the number and density of metenkephalin receptors by intermittently blocking opiate receptors. (I. S. Zagon & P. J. McLaughlin, "Naltrexone modulates tumor response in mice with neuroblastoma", Science, 221: 671-3 (12 Aug. 1983). This increase in metenkephalin is believed to enhance homeostatic regulation of the natural immune function of the human body.

In view of Zagon's findings, Bernard Bihari reported the use of low dose naltrexone for the treatment of patients with AIDS (U.S. Pat. No. 4,888,346) and herpes (U.S. Pat. No. 5,356,900). Further, Nicholas Plotnikoff reported the use of low dose naltrexone for the treatment of herpes, HIV infection, cytomegalovirus, coronavirus, influenza A and Japanese encephalitis. (E. A. Moore & S. Wilkinson, THE PROMISE OF LOW DOSE NALTREXONE THERAPY: POTENTIAL BENEFITS IN CANCER, AUTOIMMUNE, NEUROLOGICAL AND INFECTIOUS DISORDERS (McFarland & Company, Inc., Publishers, 2009)).

SUMMARY OF THE INVENTION

In one embodiment, the invention encompasses methods for treating a skin condition caused by a human papillomavirus infection comprising topically administering to a subject in need thereof an effective amount of an opioid antagonist or a pharmaceutically acceptable salt thereof.

In another embodiment, the invention encompasses kits comprising a unit dose of an opioid antagonist and a label or printed instructions instructing the topical administration of the opioid antagonist to treat a skin condition caused by a human papillomavirus infection.

In another embodiment, the invention encompasses topical compositions comprising: naltrexone in an amount of about 0.5% to about 2% by weight of the composition; an emulsifying agent in an amount of about 2% to about 5% by weight of the composition; a stiffening agent in an amount of about 2% to about 5% by weight of the composition; and an emollient in an amount of about 15% to about 30% by weight of the composition. In some embodiments, the composition is in the form of a cream.

In another embodiment, the invention encompasses topical compositions comprising: naltrexone in an amount of about 0.5% to about 2% by weight of the composition; an emulsifying agent in an amount of about 2% to about 5% by weight of the composition; a preservative in an amount of about 0.01% to about 0.6% by weight of the composition; and an emollient. In some embodiments, the composition is in the form of an ointment.

In another embodiment, the invention encompasses topical compositions comprising: naltrexone in an amount of about 0.5% to about 2% by weight of the composition; a rheology modifier or thickener in an amount of about 1% to about 2% by weight of the composition; an alkalizing or buffering agent in an amount of about 0.5% to about 5% by weight of the composition; and a solvent. In some embodiments, the composition is in the form of a gel.

DETAILED DESCRIPTION OF THE INVENTION

The present invention provides methods for treating skin conditions comprising topically administering to a subject in need thereof an effective amount of an opioid antagonist or a pharmaceutically acceptable salt thereof.

As used herein, an "effective amount" is an amount effective for treating a skin condition.

As used herein, the term "treating" a skin condition in a subject refers to subjecting the subject to a pharmaceutical treatment, e.g., the administration of one or more agents, such that at least one symptom of the condition is decreased or prevented from worsening.

Typically the skin condition to be treated is a skin condition caused by a human papillomavirus infection, or any subtype thereof. Skin conditions caused by a human papillomavirus infection include, but are not limited to, warts, lesions, and epidermodysplasia verruciformis.

Warts, also known as verruca, are common, benign epidermal lesions that can appear anywhere on the body in a variety of morphologies. They are almost universal in the population and affect all ages but are most common among children. Although warts are considered as a benign infection, they can sometimes be contagious or cause great discomfort depending on their appearance and location. Trauma and maceration facilitate initial epidermal inoculation of human papillomavirus. Local and systemic immune factors appear to influence spread and immunosuppressed patients are at particular risk of developing generalized lesions that are difficult to treat. Many warts regress spontaneously after a few months but other can persist for years and recur at the same or different sites even with treatment.

In one embodiment, the skin condition is a wart. The wart may be a common wart (verruca vulgaris), flat wart (verruca plana), palmar wart, plantar wart (verruca pedis), mosaic wart, perinungal wart, or genital wart (verruca acuminata).

Suitable opioid antagonists include compounds that block one or more opioid receptors. In some embodiments, the opioid antagonist selectively blocks the mu (μ) opioid receptor, the delta (δ) opioid receptor, or the kappa (κ) opioid receptor. In other embodiments, the opioid antagonist is non-selective. Examples of opioid antagonists include, but are not limited to, naltrexone, naloxone, nalorphine, levallorphan, nalmefene, cyprodime, naltindole, and norbinaltorphimine. In one embodiment, the opioid antagonist is naltrexone. In another embodiment, the opioid antagonist is naloxone.

In some embodiments, the opioid antagonist is a compound that may exist in the form of one or more stereoisomers, wherein one or more of those stereoisomers is therapeutically active. In some embodiments, the opioid antagonist comprises a therapeutically active stereoisomer that is substantially free of other stereoisomers. In other embodiments, the opioid antagonist comprises a therapeutically active stereoisomer that has less than about 50%, less than about 40%, less than about 30%, less than about 20%, less than about 10%, less than about 5%, or less than about 1% by weight of other steroisomers.

The opioid antagonist is typically administered to the subject in the form of a composition for topical administration. In some embodiments, the composition comprises an effective amount of the opioid antagonist and at least one pharmaceutically acceptable excipient.

In some embodiments, the opioid antagonist is present in an amount of about 0.1% to about 5% by weight of the composition. In other embodiments, the opioid antagonist is present in an amount of about 0.5% to about 4%, about 0.5% to about 2%, about 0.5% to about 1.5%, about 1% to about 4%, about 1% to about 3%, about 1% to about 2%, about 2% to about 3%, about 2% to about 4%, about 3% to about 4%, or about 1% by weight of the composition.

The pharmaceutically acceptable excipient may be any topically acceptable non-transdermally effective excipient known by those skilled in the art. Suitable excipients include, but are not limited to, emulsifying agents, stiffening agents, rheology modifiers or thickeners, surfactants, emollients, preservatives, humectants, alkalizing or buffering agents, and solvents.

Suitable emulsifying agents include, but are not limited to cetyl alcohol, cetostearyl alcohol, stearyl alcohol, carboxypolymethylene, polycarbophil, polyethylene glycol, and sorbitan esters. Suitable stiffening agents include, but are not limited to stearyl alcohol, cetostearyl alcohol, and cetyl alcohol. Suitable rheology modifiers or thickeners include, but are not limited to, carbomers such as Carbopol®, and polyoxyethylene tallow amines such as Ethomeen®. Suitable surfactants include, but are not limited to, anionic, cationic, amphoteric, and nonionic surfactants. In some embodiments, the surfactant is sodium lauryl sulfate, cetostearyl alcohol, cetyl alcohol, magnesium lauryl sulfate, a wax, or a combination thereof. Suitable emollients include, but are not limited to, white petrolatum (white vaseline), liquid petrolatum (liquid vaseline), paraffin, or aquaphor. Suitable preservatives include, but are not limited to, antimicrobial preservatives such as nipagin (methyl hydroxybenzoate), nipasol (hydroxybenzoate), butylparaben, ethylparaben, methylparaben, propyl paraben potassium, and propyl paraben sodium. Suitable humectants include, but are not limited to, propylene glycol and propylene glycol alginate. Suitable alkalizing or buffering agents include, but are not limited to, sodium hydroxide and potassium hydroxide. Suitable solvents include, but are not limited to, water.

The composition may be in the form of a gel, cream, ointment, liquid, suspension, solution, emulsion, foam, aerosol or the like for topical administration. Typically, the composition is administered to the subject by spreading (e.g., gel, cream, or ointment) or spraying (e.g., liquid or aerosol) onto the affected area of the skin.

In one embodiment, the composition is in the form of a cream. Typically, the cream comprises an opioid antagonist and one or more of an emulsifying agent, a stiffening agent, a surfactant, an emollient, a preservative, a humectant, an alkalizing or buffering agent, and a solvent. In some embodiments, the cream has a formulation according to Table 1a, 1b, or 1c.

TABLE 1a

Illustrative Cream Formulation

| Ingredient | Amount (% by weight of the composition) |
|---|---|
| Opioid antagonist | about 0.1%-5% |
| Emulsifying agent | about 2%-5% |
| Stiffening agent | about 1%-45% |
| Surfactant | about 0.5%-2.5% |
| Preservative | about 0.01%-0.6% |
| Humectant | about 1%-15% |
| Alkalizing or buffering agent | about 0.01%-3% |
| Emollient | about 1%-50% |
| Solvent | q.s |

TABLE 1b

Illustrative Cream Formulation

| Ingredient | Amount (% by weight of the composition) |
|---|---|
| Opioid antagonist | about 0.5%-2% |
| Emulsifying agent | about 2%-5% |
| Stiffening agent | about 2%-5% |
| Surfactant | about 0.5%-1.5% |
| Preservative | about 0.01%-0.6% |
| Humectant | about 2%-10% |
| Alkalizing or buffering agent | about 0.01%-3% |
| Emollient | about 15%-30% |
| Solvent | q.s |

TABLE 1c

Illustrative Cream Formulation

| Ingredient | Amount (% by weight of the composition) |
| --- | --- |
| Opioid antagonist | about 0.5%-2% |
| Cetyl alcohol and/or carboxypolymethylene | about 2%-5% |
| Stearyl alcohol | about 2%-5% |
| Sodium lauryl sulfate | about 0.5%-1.5% |
| Nipagin and/or Nipasol | about 0.01%-0.6% |
| Propylene glycol | about 2%-10% |
| Sodium hydroxide | about 0.01%-3% |
| White vaseline and/or liquid vaseline | about 15%-30% |
| Water | q.s |

In one embodiment, the composition is in the form of an ointment. Typically, the ointment comprises an opioid antagonist and one or more of an emulsifying agent, an emollient, and a preservative. In some embodiments, the ointment has a formulation according to Table 2a, 2b, or 2c.

TABLE 2a

Illustrative Ointment Formulation

| Ingredient | Amount (% by weight of the composition) |
| --- | --- |
| Opioid antagonist | about 0.1%-5% |
| Emulsifying agent | about 1%-10% |
| Preservative | about 0.01%-0.6% |
| Emollient | q.s. |

TABLE 2b

Illustrative Ointment Formulation

| Ingredient | Amount (% by weight of the composition) |
| --- | --- |
| Opioid antagonist | about 0.5%-2% |
| Emulsifying agent | about 2%-5% |
| Preservative | about 0.01%-0.6% |
| Emollient | q.s. |

TABLE 2c

Illustrative Ointment Formulation

| Ingredient | Amount (% by weight of the composition) |
| --- | --- |
| Opioid antagonist | about 0.5%-2% |
| Polyoxyethylene 20 sorbitan monooleate | about 2%-5% |
| Nipagin and/or Nipasol | about 0.01%-0.6% |
| White vaseline and/or liquid vaseline | q.s. |

In one embodiment, the composition is in the form of a gel. Typically, the gel comprises an opioid antagonist and one or more of a rheology modifier or thickener, an alkalizing or buffering agent, and a solvent. In some embodiments, the gel has a formulation according to Table 3a, 3b, or 3c.

TABLE 3a

Illustrative Gel Formulation

| Ingredient | Amount (% by weight of the composition) |
| --- | --- |
| Opioid antagonist | about 0.1%-5% |
| Rheology modifier or thickener | about 0.5%-2% |
| Alkalizing or buffering agent | about 0.5%-10% |
| Solvent | q.s. |

TABLE 3b

Illustrative Gel Formulation

| Ingredient | Amount (% by weight of the composition) |
| --- | --- |
| Opioid antagonist | about 0.5%-2% |
| Rheology modifier or thickener | about 1%-2% |
| Alkalizing or buffering agent | about 0.5%-5% |
| Solvent | q.s |

TABLE 3c

Illustrative Gel Formulation

| Ingredient | Amount (% by weight of the composion) |
| --- | --- |
| Opioid antagonist | about 0.5%-2% |
| Carbomer | about 1%-2% |
| Sodium hydroxide | about 0.5%-5% |
| Water | q.s |

The composition may be administered to the subject daily, every other day, three times a week, twice a week, once a week, or at other appropriate intervals. In some embodiments, the composition is administered until there is complete healing of the skin condition in the affected area.

The present invention may use lower doses of opioid antagonist than the doses conventionally used for oral administration in the treatment of alcohol or narcotic addiction. The opioid antagonist is administered to the individual in an amount effective to treat the skin condition. In certain embodiments, the exact dose of opioid antagonist depends upon, by way of non-limiting example, the form in which the opioid antagonist is administered, the subject to be treated, the age, body weight and/or height of the subject to be treated, the preference and experience of the attending physician, the specific opioid antagonist used, the characteristics of the patient, and/or the nature of the skin condition for which the treatment is sought. Thus, in some embodiments, the dosage of opioid antagonist administered may vary from those disclosed herein. In various embodiments, these factors are determined by those of skill in the medical and pharmaceutical arts in view of the present disclosure.

Typically, the opioid antagonist is administered to the subject in a total daily dose of up to about 150 mg/cm$^2$ of skin. In some embodiments, the opioid antagonist is administered to the subject in a total daily dose of about 5 mg/cm$^2$ of skin to about 150 mg/cm$^2$ of skin, about 10 mg/cm$^2$ of skin to about 100 mg/cm$^2$ of skin, about 20 mg/cm$^2$ of skin to about 90 mg/cm$^2$ of skin, about 30 mg/cm$^2$ of skin to about 80 mg/cm$^2$ of skin, about 40 mg/cm$^2$ of skin to about 70 mg/cm$^2$ of skin, or about 50 mg/cm$^2$ of skin or about 60 mg/cm$^2$ of skin. The total daily dose may be delivered once per day, or divided between multiple doses. In some embodiments, the opioid antagonist is administered 1, 2, 3, 4, or 5 times per day.

The methods of the invention may further comprise administration of one or more additional agents effective to treat the skin condition. Where the skin condition is warts, the additional agent may include, but not be limited to, salicylic acid, trichloroacetic acid, 5-fluorouracil, tretinoin, antharidin, podophyllum resin, imiquinod, cidofovir, cimetidine, isotretinoin, oral zinc, bleomycin, interferon α-2β, or contact immunotherapy. The additional agent and the opioid antagonist may be administered concurrently or separately. When administered concurrently, the additional agent and the opioid antagonist may be administered in the same or separate compositions.

In addition, treatment with opioid antagonists as described herein can be used before, after, or concurrently with traditional "destructive" wart treatments, such as cryosurgery, electrocautery, curettage, excision, or laser methods.

In another embodiment, the invention encompasses kits comprising a unit dose of opioid antagonist. In one embodiment the unit dose is within a container, which can be sterile, containing an effective amount of opioid antagonist and a pharmaceutically acceptable excipient. The kits can further comprise a label or printed instructions instructing the use of the opioid antagonist to treat a skin condition. The kits can further comprise a device that is useful for administering the unit dose as described herein. Examples of such a device include, but are not limited to, a wand, a dropper, a cotton swab, a pad, or the like.

Having described the invention with reference to certain embodiments, other embodiments will become apparent to one skilled in the art from consideration of the specification. The invention is further defined by reference to the following examples. It will be apparent to those skilled in the art that many modifications, both to materials and methods, may be practiced without departing from the scope of the invention.

EXAMPLES

Example 1

Treatment of Common Warts with Naltrexone 100 g of naltrexone 1% cream was prepared by mixing 1 g of naltrexone hydrochloride in 99 g of a cream base containing the following excipients: cetyl alcohol, stearyl alcohol, sodium lauryl sulfate, vaseline, nipagin, nipasol, carboxypolymethylene, propyleneglycol, sodium hydroxide and distilled water.

a. 52 Year Old Man

A 52 year old man with a recurrent common wart of 3 mm diameter located on the top of his right hand was treated with the 1% naltrexone cream described above. The naltrexone cream was administered to the affected area three times daily (morning, noon, and evening) in a total daily amount of 1 g, and the wart regressed and completely disappeared after 15 days of treatment. No side effects were observed and additional treatment was unnecessary.

b. 40 Year Old Woman

A 40 year old woman with a new common wart of 3-4 mm diameter located on a finger of her right hand was treated with the 1% naltrexone cream described above. The naltrexone cream was administered to the affected area three times daily (morning, noon, and evening) in a total daily amount of 1 g, and the wart regressed and completely disappeared after 9 days of treatment. No side effects were observed and additional treatment was unnecessary.

c. 10 Year Old Boy

A 10 year old boy with two new common warts of 3 mm diameter located on his fourth and fifth toes of his right foot was treated with the 1% naltrexone cream described above. The naltrexone cream was administered to the affected area once daily in a total daily amount of 0.4 g for the first week of treatment. During the second week of treatment, the naltrexone cream was administered to the affected area three times daily (morning, noon, and evening) in a total daily amount of 1 g. The wart on the fourth toe regressed and completely disappeared and the warts on the fifth toe regressed significantly after 2 weeks of treatment. No side effects were observed and additional treatment was unnecessary.

Example 2

Naltrexone Formulations

The following are illustrative naltrexone formulations according to the present invention.

TABLE 4

Illustrative Naltrexone Cream Formulation

| Ingredient | Amount (% by weight of the composition) |
|---|---|
| Naltrexone | 1% |
| Cetyl alcohol | 3.6% |
| Stearyl alcohol | 3.6% |
| Sodium lauryl sulfate | 0.8% |
| Nipagin | 0.1% |
| Nipasol | 0.05% |
| Carboxylpolymethylene | 0.2% |
| Propylene glycol | 5% |
| Sodium hydroxide | 0.03% |
| White vaseline | 13.5% |
| Liquid vaseline | 5.4% |
| Water | q.s |

TABLE 5

Illustrative Naltrexone Ointment Formulation

| Ingredient | Amount (% by weight of the composition) |
|---|---|
| Naltrexone | 1% |
| Polyoxyethylene 20 sorbitan monooleate | 4% |
| Nipagin | 0.18% |
| Nipasol | 0.02% |
| White vaseline | 10% |
| Liquid vaseline | q.s. |

TABLE 6

Illustrative Naltrexone Gel Formulation

| Ingredient | Amount (% by weight of the composition) |
|---|---|
| Naltrexone | 1% |
| Carbomer | 2% |
| Sodium hydroxide | 1.25% |
| Water | q.s |

We claim:
1. A kit comprising:
a) a unit dose comprising:
   naltrexone present in 1% by weight of the unit dose;
   cetyl alcohol present in 3.6% by weight of the unit dose;
   stearyl alcohol present in 3.6% by weight of the unit dose;
   sodium lauryl sulfate present in 0.8% by weight of the unit dose;

nipagin present in 0.1% by weight of the unit dose;
nipasol present in 0.05% by weight of the unit dose;
carboxylpolymethylene present in 0.2% by weight of the unit dose;
propylene glycol present in 5% by weight of the unit dose;
sodium hydroxide present in 0.03% by weight of the unit dose;
white vaseline present in 13.5% by weight of the unit dose;
liquid vaseline present in 5.4% by weight of the unit dose; and
an amount of water sufficient to provide a total of 100% weight for the unit dose; and,
b) a label or printed instructions instructing the topical administration of the unit dose to treat a skin condition caused by a human papillomavirus infection.

2. The kit of claim 1, further comprising a device that is useful for topically administering the unit dose.

3. The kit of claim 1, wherein the skin condition is a wart or a lesion.

4. The kit of claim 3, wherein the wart is a common wart, flat wart, palmar wart, plantar wart, mosaic wart, perinungal wart, or genital wart.

5. The kit of claim 1, wherein the unit dose is in the form of a cream.

6. A topical composition comprising:
naltrexone present in 1% by weight of the composition;
cetyl alcohol present in 3.6% by weight of the composition;
stearyl alcohol present in 3.6% by weight of the composition;
sodium lauryl sulfate present in 0.8% by weight of the composition;
nipagin present in 0.1% by weight of the composition;
nipasol present in 0.05% by weight of the composition;
carboxylpolymethylene present in 0.2% by weight of the composition;
propylene glycol present in 5% by weight of the composition;
sodium hydroxide present in 0.03% by weight of the composition;
white vaseline present in 13.5% by weight of the composition;
liquid vaseline present in 5.4% by weight of the composition; and
an amount of water sufficient to provide a total of 100% weight for the composition.

7. The topical composition of claim 6, wherein the topical composition is in the form of a cream.

8. A topical composition consisting essentially of:
naltrexone present in 1% by weight of the composition;
cetyl alcohol present in 3.6% by weight of the composition;
stearyl alcohol present in 3.6% by weight of the composition;
sodium lauryl sulfate present in 0.8% by weight of the composition;
nipagin present in 0.1% by weight of the composition;
nipasol present in 0.05% by weight of the composition;
carboxylpolymethylene present in 0.2% by weight of the composition;
propylene glycol present in 5% by weight of the composition;
sodium hydroxide present in 0.03% by weight of the composition;
white vaseline present in 13.5% by weight of the composition;
liquid vaseline present in 5.4% by weight of the composition; and
an amount of water sufficient to provide a total of 100% weight for the composition.

9. The topical composition of claim 8, wherein the topical composition is in the form of a cream.

10. A method for treating a skin condition caused by a human papillomavirus infection comprising topically administering to a subject in need thereof an effective amount of the composition of claim 6.

11. A method for treating a skin condition caused by a human papillomavirus infection, the method comprising topically administering to a subject in need thereof an effective amount of a topical composition comprising:
naltrexone present in 1% by weight of the composition;
cetyl alcohol present in 3.6% by weight of the composition;
stearyl alcohol present in 3.6% by weight of the composition;
sodium lauryl sulfate present in 0.8% by weight of the composition;
nipagin present in 0.1% by weight of the composition;
nipasol present in 0.05% by weight of the composition;
carboxylpolymethylene present in 0.2% by weight of the composition;
propylene glycol present in 5% by weight of the composition;
sodium hydroxide present in 0.03% by weight of the composition;
white vaseline present in 13.5% by weight of the composition;
liquid vaseline present in 5.4% by weight of the composition; and
an amount of water sufficient to provide a total of 100% weight for the composition.

12. The method of claim 11, wherein the naltrexone has less than about 10% by weight of other stereoisomers.

13. The method of claim 11, wherein the naltrexone has less than about 5% by weight of other stereoisomers.

14. The method of claim 11, wherein the skin condition is a wart or a lesion.

15. The method of claim 14, wherein the wart is a common wart, flat wart, palmar wart, plantar wart, mosaic wart, perinungal wart, or genital wart.

16. The method of claim 11, wherein the composition is in the form of a cream.

17. The method of claim 11, wherein the composition is administered to the subject by spreading or spraying the composition onto an affected area of the skin.

18. The method of claim 11, wherein the composition is administered 1, 2, 3, 4, or 5 times daily.

19. The method of claim 11, wherein the composition is administered in an effective amount to deliver a total daily dose of naltrexone up to about 150 mg/cm$^2$ of skin.

20. The method of claim 1, wherein the composition is administered in an effective amount to deliver a total daily dose of naltrexone about 10 mg/cm$^2$ to about 100 cm$^2$ of skin.

21. The method of claim 11, wherein the composition is administered in an effective amount to deliver a total daily dose of naltrexone about 50 mg/cm$^2$ of skin.

22. The method of claim 11, further comprising administering to the subject one or more additional agents effective to treat the skin condition.

* * * * *